US012569428B2

(12) United States Patent
Kondo et al.

(10) Patent No.: US 12,569,428 B2
(45) Date of Patent: Mar. 10, 2026

(54) OIL-IN-WATER CLEANSING COSMETIC COMPOSITION

(71) Applicant: DOW TORAY CO., LTD., Tokyo (JP)

(72) Inventors: Junya Kondo, Tokyo (JP); Yasue Kanzaki, Ichihara (JP); Son Thanh Phan, Ichihara (JP); Jun Miyano, Tokyo (JP); Sayuri Kikunaga, Ichihara (JP); Seiji Hori, Ichihara (JP)

(73) Assignee: DOW TORAY CO., LTD., Tokyo (JP)

( * ) Notice: Subject to any disclaimer, the term of this patent is extended or adjusted under 35 U.S.C. 154(b) by 769 days.

(21) Appl. No.: 17/601,530

(22) PCT Filed: Jul. 31, 2019

(86) PCT No.: PCT/JP2019/029927
§ 371 (c)(1),
(2) Date: Oct. 5, 2021

(87) PCT Pub. No.: WO2020/208838
PCT Pub. Date: Oct. 15, 2020

(65) Prior Publication Data

US 2022/0183956 A1 Jun. 16, 2022

(30) Foreign Application Priority Data

Apr. 10, 2019 (JP) ................................ 2019-074793

(51) Int. Cl.
*A61K 8/891* (2006.01)
*A61K 8/06* (2006.01)
*A61K 8/34* (2006.01)
*A61Q 1/14* (2006.01)

(52) U.S. Cl.
CPC .............. *A61K 8/891* (2013.01); *A61K 8/062* (2013.01); *A61K 8/345* (2013.01); *A61Q 1/14* (2013.01)

(58) Field of Classification Search
CPC .............. A61K 8/19; A61K 8/31; A61K 8/44; A61K 8/062; A61K 8/345; A61K 8/891; A61Q 1/14; C08G 77/04; C08G 77/14; C08G 77/46; C08K 5/06; C08L 83/00; C08L 83/06; C08L 83/12
See application file for complete search history.

(56) References Cited

U.S. PATENT DOCUMENTS

| | | | | |
|---|---|---|---|---|
| 4,501,619 | A | 2/1985 | Gee | |
| 4,744,978 | A | 5/1988 | Homan et al. | |
| 4,844,888 | A | 7/1989 | Zawadzki | |
| 4,980,167 | A | 12/1990 | Harashima et al. | |
| 5,596,061 | A | 1/1997 | Berger et al. | |
| 5,628,989 | A | 5/1997 | Harashima et al. | |
| 5,643,380 | A | 7/1997 | Saitoh et al. | |
| 5,939,478 | A | 8/1999 | Beck et al. | |
| 5,948,391 | A | 9/1999 | O'Lenick, Jr. | |
| 6,238,656 | B1 | 5/2001 | Morita et al. | |
| 6,290,941 | B1 | 9/2001 | Lahanas et al. | |
| 6,342,209 | B1 | 1/2002 | Patil et al. | |
| 6,384,104 | B1 | 5/2002 | Chang et al. | |
| 7,981,405 | B2 | 7/2011 | Ueyama et al. | |
| 8,500,900 | B2 | 8/2013 | Sugiura et al. | |
| 8,900,553 | B2 | 12/2014 | Tamarkin et al. | |
| 8,956,449 | B2 | 2/2015 | Kojima et al. | |
| 9,486,652 | B2 | 11/2016 | Araki et al. | |
| 10,130,579 | B2 | 11/2018 | Kanaya et al. | |
| 12,023,403 | B2 * | 7/2024 | Kanzaki | A61K 8/8152 |
| 2002/0031488 | A1 | 3/2002 | Kanji et al. | |
| 2003/0212232 | A1 | 11/2003 | Majeti et al. | |
| 2009/0253885 | A1 | 10/2009 | Kamei | |
| 2010/0189676 | A1 | 7/2010 | Matsuzawa et al. | |
| 2010/0190871 | A1 | 7/2010 | Araki et al. | |
| 2010/0216744 | A1 | 8/2010 | Mizutani et al. | |
| 2010/0317555 | A1 | 12/2010 | Araki et al. | |
| 2011/0182846 | A1 | 7/2011 | Ikeda et al. | |
| 2012/0040931 | A1 | 2/2012 | Kamei | |
| 2012/0251605 | A1 | 10/2012 | Iimura et al. | |
| 2012/0263662 | A1 | 10/2012 | Iimura et al. | |
| 2014/0199251 | A1 | 7/2014 | Ashida et al. | |

(Continued)

FOREIGN PATENT DOCUMENTS

| | | | |
|---|---|---|---|
| CN | 104125973 | A | 10/2014 |
| EP | 2997956 | A1 | 3/2016 |

(Continued)

OTHER PUBLICATIONS

Machine assisted English translation of JP2017178930A obtained from https://patents.google.com/patent on Oct. 26, 2021, 11 pages.
Machine assisted English translation of JP2016185932A obtained from https://patents.google.com/patent on Oct. 26, 2021, 12 pages.
Machine assisted English translation of WO2015125332A1 obtained from https://patents.google.com/patent on Oct. 26, 2021, 11 pages.
Machine assisted English Translation of JP2002275265A obtained from https://worldwide.espacenet.com on May 2, 2024, 20 pages.
Machine assisted English Translation of JPH01261316 obtained from https://worldwide.espacenet.com on May 3, 2021, 8 pages.
Machine assisted English Translation of JPH1143417 obtained from https://worldwide.espacenet. com on May 4, 2021, 13 pages.
Machine assisted English Translation of JP2002322015A obtained from https://worldwide.espacenet.com on Dec. 11, 2023, 15 pages.
Machine assisted English Translation of JP2002146188A obtained from https://worldwide.espacenet.com on Dec. 11, 2023, 13 pages.
Machine assisted English translation of JP2011073971A obtained from https://patents.google.com/patent on Oct. 18, 2021, 9 pages.

(Continued)

*Primary Examiner* — Hong Yu
(74) *Attorney, Agent, or Firm* — Warner Norcross + Judd LLP

(57) ABSTRACT

Provided is an oil-in-water cleansing cosmetic composition. The oil-in-water cleansing cosmetic composition comprises: (A) carboxylic acid-modified silicone that is liquid at 50° C.; (B) 3 to 80 mass % of an oil agent relative to the total mass of the cosmetic composition; (C) water; and (D) a basic compound. An amount of an ionic surfactant other than the carboxylic acid-modified silicone (A) that is liquid at 50° C. is 10 mass % or less relative to the total mass of the cosmetic composition. In general, the oil-in-water cleansing cosmetic composition quickly blends with makeup grime, has a high makeup removing effect, and has excellent stability.

14 Claims, No Drawings

(56) References Cited

U.S. PATENT DOCUMENTS

| | | | | |
|---|---|---|---|---|
| 2014/0235732 | A1 | 8/2014 | Ibe et al. | |
| 2014/0255323 | A1 | 9/2014 | Ishida et al. | |
| 2014/0348765 | A1 | 11/2014 | Sasaki | |
| 2015/0011656 | A1 | 1/2015 | Tamura et al. | |
| 2015/0157546 | A1 | 6/2015 | Naoi | |
| 2015/0174054 | A1* | 6/2015 | Chiou | A61K 8/891 514/772.3 |
| 2015/0216787 | A1 | 8/2015 | Hori et al. | |
| 2015/0232601 | A1 | 8/2015 | Furukawa et al. | |
| 2016/0120786 | A1 | 5/2016 | Halpern Chirch et al. | |
| 2017/0035681 | A1* | 2/2017 | Kanaya | A61Q 1/00 |
| 2017/0304658 | A1 | 10/2017 | Roudot et al. | |
| 2018/0215877 | A1 | 8/2018 | Hori et al. | |
| 2018/0263883 | A1 | 9/2018 | Uyama et al. | |
| 2019/0053999 | A1 | 2/2019 | Hori et al. | |
| 2019/0144612 | A1 | 5/2019 | Hori et al. | |
| 2019/0231674 | A1 | 8/2019 | Furukawa et al. | |
| 2021/0244641 | A1 | 8/2021 | Kondo et al. | |
| 2021/0322296 | A1 | 10/2021 | Kikunaga et al. | |
| 2021/0330559 | A1 | 10/2021 | Kondo et al. | |
| 2022/0183955 | A1 | 6/2022 | Kondo et al. | |
| 2022/0183956 | A1 | 6/2022 | Kondo et al. | |
| 2022/0257497 | A1 | 8/2022 | Kanzaki et al. | |

FOREIGN PATENT DOCUMENTS

| | | | |
|---|---|---|---|
| EP | 3132789 | A1 | 2/2017 |
| EP | 3213742 | A1 | 9/2017 |
| EP | 3327064 | A1 | 5/2018 |
| EP | 3838249 | A1 | 6/2021 |
| EP | 3838255 | A1 | 6/2021 |
| EP | 3838256 | A1 | 6/2021 |
| JP | S62103007 | A | 5/1987 |
| JP | H01261316 | A | 10/1989 |
| JP | H02243612 | A | 9/1990 |
| JP | H0812524 | A | 1/1996 |
| JP | H0812545 | A | 1/1996 |
| JP | H0812546 | A | 1/1996 |
| JP | H0844260 | A | 2/1996 |
| JP | H08109263 | A | 4/1996 |
| JP | H08157335 | A | 6/1996 |
| JP | H0959125 | A | 3/1997 |
| JP | H09241511 | A | 9/1997 |
| JP | H1143417 | A | 2/1999 |
| JP | H11504665 | A | 4/1999 |
| JP | H11193331 | A | 7/1999 |
| JP | 2000281523 | A | 10/2000 |
| JP | 2001172463 | A | 6/2001 |
| JP | 2002114849 | A | 4/2002 |
| JP | 2002146188 | A | 5/2002 |
| JP | 2002146189 | A | 5/2002 |
| JP | 2002275265 | A | 9/2002 |
| JP | 2002293726 | A | 10/2002 |
| JP | 2002322015 | A | 11/2002 |
| JP | 2004026669 | A | 1/2004 |
| JP | 2004091423 | A | 3/2004 |
| JP | 2005524747 | A | 8/2005 |
| JP | 2007277415 | A | 10/2007 |
| JP | 2009185144 | A | 8/2009 |
| JP | 2009263643 | A | 11/2009 |
| JP | 2010138074 | A | 6/2010 |
| JP | 2011073971 | A | 4/2011 |
| JP | 2011148784 | A | 8/2011 |
| JP | 2011149017 | A | 8/2011 |
| JP | 2012036348 | A | 2/2012 |
| JP | 2013121947 | A | 6/2013 |
| JP | 2013144655 | A | 7/2013 |
| JP | 2013177370 | A | 9/2013 |
| JP | 2014040511 | A | 3/2014 |
| JP | 2014040512 | A | 3/2014 |
| JP | 2014201569 | A | 10/2014 |
| JP | 2015203026 | A | 11/2015 |
| JP | 2016185932 | A | 10/2016 |
| JP | 2017178930 | A | 10/2017 |
| JP | 2018024881 | | 2/2018 |
| JP | 2018115211 | A | 7/2018 |
| WO | 1995023579 | A2 | 9/1995 |
| WO | 2009022621 | A1 | 2/2009 |
| WO | 2009025146 | A1 | 2/2009 |
| WO | 2012070309 | A1 | 5/2012 |
| WO | 2013061776 | A1 | 5/2013 |
| WO | 2013100177 | A1 | 7/2013 |
| WO | 2013108515 | A1 | 7/2013 |
| WO | 2013115099 | A1 | 8/2013 |
| WO | 2014185316 | A1 | 11/2014 |
| WO | 2015125332 | A1 | 8/2015 |
| WO | 2017018358 | A1 | 2/2017 |
| WO | 2017061090 | A1 | 4/2017 |
| WO | 2017191798 | A1 | 11/2017 |
| WO | 2018066559 | A1 | 4/2018 |
| WO | 2020036061 | A1 | 2/2020 |
| WO | 2020036062 | A1 | 2/2020 |
| WO | 2020036063 | A1 | 2/2020 |
| WO | 2020036064 | A1 | 2/2020 |
| WO | 2020036065 | A1 | 2/2020 |

OTHER PUBLICATIONS

Machine assisted English Translation of JP2013177370 obtained from https://worldwide.espacenet.com on May 3, 2021, 18 pages.
Machine assisted English Translation of JP2014201569 obtained from https://worldwide. espacenet.com on May 3, 2021, 25 pages.
Machine assisted English Translation of JP2018115211 obtained from https://worldwide.espacenet.com on May 3, 2021, 41 pages.
Machine assisted English Translation of WO2013115099 obtained from https://worldwide.espacenet.com on May 3, 2021, 36 pages.
Machine assisted English translation of JP2004091423A obtained from https://patents.google.com/patent on Oct. 18, 2021, 5 pages.
Machine assisted English translation of JP2002293726A obtained from https://patents.google.com/patent on Oct. 18, 2021, 11 pages.
Machine assisted English translation of JP2002146189A obtained from https://patents.google.com/patent on May 26, 2022, 11 pages.
Momentive "SilFormâ„¢ INX Fluid"—Marketing Bulletin, obtained from https://www.momentive.com/docs/default-source/productdocuments/silform-inx-fluid/silform-inx-fluid-marketing-bulletin-(1)20956cf16e974c2d9a951e587eee27dc.pdf, 12 pages.
Cassiday www.aocs.org/stay-informed/inform-magazine/featured-articles/emulsions-making-oil-and-water-mix-april2014?SSO=True# (Year: 2014).
PCT/JP2015/060963 International Search Report dated Jul. 14, 2015, 2 pages.
English language abstract and machine translation for JPH0812524(A) extracted from http://worldwide.espacenet.com database on Oct. 25, 2016, 13 pages.
English language abstract and machine translation for JPH0812546 (A) extracted from http://worldwide.espacenet.com database on Oct. 25, 2016, 12 pages.
English language abstract and machine translation for JPH08109263 (A) extracted from http://worldwide. espacenet. com database on Oct. 25, 2016, 24 pages.
English language abstract and machine translation for JPH09241511 (A) extracted from http://worldwide. espacenet. com database on Oct. 25, 2016, 13 pages.
English language abstract and machine translation for JP2002114849 (A) extracted from http://worldwide.espacenet. com database on Oct. 25, 2016, 10 pages.
English language abstract and machine translation for JP2004026669 (A) extracted from http://worldwide.espacenet. com database on Oct. 25, 2016, 12 pages.
Machine assisted English translation of WO2012070309A1 obtained from https://patents.google.com/patent on Aug. 8, 2024, 8 pages.
K. Kageshima et al., Fragrance Journal, Special Issue Nov. 19, 2005, p. 125-130.
English language abstract for JP2010138074 (A) extracted from http://worldwide.espacenet.com database on Oct. 25, 2016 and machine translation extracted from https://patents.google.com database on Jan. 13, 2017, 20 pages.

(56) References Cited

OTHER PUBLICATIONS

English language abstract and machine translation for JP2007277415 (A) extracted from http://worldwide.espacenet.com database on Jun. 4, 2018, 29 pages.
Machine assisted English translation of JP2000281523A obtained from <https://patents.google.com/patent> on Aug. 8, 2024, 16 pages.
English translation of International Search Report for PCT/JP2019/029957 dated Oct. 8, 2019, 2 pages.
Momentive: "Silform INX fluid", Internet Citation, Feb. 2, 2015 (Feb. 2, 2015), XP002785508, Retrieved from the Internet: URL:http://www.essentialingredients.com/pdf/SilFormINXmarketingbrochure.pdf.
Database GNPD [Online] Mintel; Oct. 29, 2012 (Oct. 29, 2012), anonymous: "Cream+", XP055907992, Database accession No. 1900229.
Database GNPD [Online] Mintel; Apr. 22, 2016 (Apr. 22, 2016), anonymous: "Ultra Sun Protection Cream SPF 50+", XP055908000, Database accession No. 3945269.
Database GNPD [Online] Mintel; Apr. 26, 2010 (Apr. 26, 2010), anonymous: "Skin Empowering Cream", XP055907993, Database accession No. 1323504.
Database GNPD [Online] Mintel; Jan. 28, 2019 (Jan. 28, 2019), anonymous: "Wrinkle Resetter", XP055907996, Database accession No. 6296569.
English Translation of International Search Report for PCT/JP2019/029956, dated Oct. 8, 2019, 2 pages.
Momentive "SilForm? INX Fluid"—Marketing Bulletin, obtained from https://www.momentive.com/docs/default-source/productdocuments/siliform-inx-fluid/silform-inx-fluid-marketing-bulletin-(1).20956cf16e974c2d9a951e587eee27dc.pdf , 12 pages 2017.
English Translation of International Search Report for PCT/JP2019/029937, dated Oct. 21, 2019, 2 pages.
English Translation of International Search Report for PCT/JP2019/029930, dated Oct. 15, 2019, 2 pages.
English Translation of International Search Report for PCT/JP2019/029958, dated Oct. 15, 2019, 1 page.
English Translation of International Search Report for PCT/JP2019/029935, dated Oct. 15, 2019, 2 pages.
International Search Report for PCT/JP2019/029927 dated Oct. 15, 2019, 2 pages.
Machine assisted English translation of JPH0959125A obtained from https://patents.google.com/patent on Nov. 25, 2024, 7 pages.

* cited by examiner

OIL-IN-WATER CLEANSING COSMETIC COMPOSITION

CROSS-REFERENCE TO RELATED APPLICATIONS

This application is the U.S. National Stage of International Application No. PCT/JP2019/029927 filed on 31 Jul. 2019, which claims priority to and all advantages of Japanese Patent Application No. 2019-074793 filed on 10 Apr. 2019, the content of which is incorporated herein by reference.

TECHNICAL FIELD

The present invention relates to an oil-in-water cleansing cosmetic composition containing a continuous aqueous phase and a discontinuous oil phase.

BACKGROUND ART

Cleansing cosmetic compositions for removing cosmetics and grime on the skin are broadly classified into so-called surfactant type and solvent type cleansing cosmetic compositions. The surfactant type removes cosmetics and grime by a cleaning action of a surfactant. With this type, the cleansing cosmetic composition is taken in the hand, lathered by adding water, and then applied to the skin to wash off cosmetics and grime, leaving no oily film feeling and leaving the cleaned skin feeling refreshed. The solvent type removes cosmetics and grime by a dissolving action of a solvent. With this type, a cleansing cosmetic composition is taken in the hand and applied directly to the skin to dissolve and disperse cosmetics and grime into a cleansing material, which is then wiped off or washed off with water (Mori and Tsurumi, "Usefulness of Cosmetic Products," pp. 66-81, Yakuji Nippo Limited, 2001). In recent years, the water resistance of makeup cosmetic compositions and sunscreen cosmetic compositions has been significantly improved, and a solvent type cleansing material is suitable for sufficiently removing such strong makeup grime. Therefore, various cleansing cosmetic compositions of this type have been developed. Oil cleansing cosmetic compositions having an oil agent as a main component are widely used as the solvent type cleansing cosmetic compositions. However, oil cleansing cosmetic compositions have a problem with stickiness and the like during and after use, and thus feel during use is inferior.

Therefore, an oil-in-water cleansing cosmetic composition containing water along with an oil agent is also provided. The oil-in-water cleansing cosmetic composition mixes with oily makeup grime by phase inverting from an O/W type to a W/O type due to water evaporation during rubbing to remove the grime. However, phase inversion requires time; therefore, when mixing with makeup grime is slow, and a high amount of oil is blended in order to facilitate a phase inversion, there is a problem where the stability and feel during use are reduced. Furthermore, the oil-in-water cleansing cosmetic composition also has a problem of generally having a lower makeup removing effect than an oil cleansing cosmetic composition.

Furthermore, Japanese Unexamined Patent Application 2009-185144 discloses a cleaning material using a carboxylic acid-modified silicone, but specifically discloses a foaming type surfactant cleaning material in which a large amount of an anionic surfactant is blended and that essentially does not contain an oil agent, which is different from the solvent cleansing cosmetic composition whose main purpose is to remove makeup.

RELATED ART DOCUMENTS

Patent Documents

Patent Document 1: Japanese Unexamined Patent Application No. 2009-185144

SUMMARY OF THE INVENTION

Problem to be Solved by the Invention

An object of the present invention is to provide an oil-in-water cleansing cosmetic composition that quickly blends with makeup grime, has a high makeup removing effect, and has excellent stability.

Means for Solving the Problem

The object of the present invention is achieved by an oil-in-water cleansing cosmetic composition containing the following components:

(A) carboxylic acid-modified silicone that is liquid at 50° C.;

(B) 3 to 80 mass % of an oil agent relative to the total mass of the cosmetic composition;

(C) water; and (D) a basic compound; where an amount of an ionic surfactant other than the carboxylic acid-modified silicone (A) that is liquid at 50° C. is 10 mass % or less relative to the total mass of the cosmetic composition.

The carboxylic acid-modified silicone (A) is preferably expressed by the following structural formula (1):

[Formula 1]

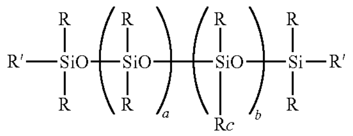

(1)

(where

Rc represents a carboxyl group-containing organic group as expressed by a general formula: $—R^1—(OR^2)p\text{-}(O)w\text{-}R^3—COOH$, ($R^1$ represents a linear or branched alkylene group having 2 to 22 carbon atoms, $R^2$ represents a linear or branched alkylene group having 2 to 4 carbon atoms, $R^3$ represents a bond (-) or a linear or branched alkylene group having 1 to 22 carbon atoms, p represents a number from 0 to 200, and w represents a number of 0 or 1, R represents the same or different alkyl or alkoxy group, having 1 to 22 carbon atoms, or phenyl group), R' is Rc or R, and a and b each represent 0 or a positive number, a+b is a number within a range of 0 to 30, and when b is 0, at least one of R' is Rc.)

The carboxylic acid modified silicone (A) is preferably liquid at room temperature (25° C.).

Furthermore, the carboxylic acid-modified silicone (A) is preferably expressed by the following structural formula (2):

[Formula 2]

(2)

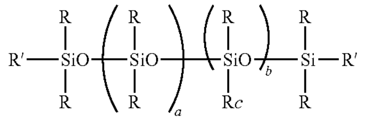

(Where

Rc represents an organic group containing a carboxyl group as expressed by general formula: —$R^1$—$(OR^2)$p-(O) w-$R^3$—COOH, ($R^1$ represents a straight chain or branched chain alkylene group having 2 to 22 carbon atoms, $R^2$ represents a straight chain or branched chain alkylene group having 2 to 4 carbon atoms, $R^3$ represents a bond (-) or a straight chain or branched chain alkylene group having 1 to 22 carbon atoms, p represents a number from 0 to 200, and w represents a number of 0 or 1), R represents the same or a different alkyl or alkoxy group, having 1 to 22 carbon atoms, or phenyl group, R' is Rc or R, and a and b each represent a positive number, a+b is a number within a range of 2 to 20, and a/b is within a range of 0.3 to 3.0.))

The oil-in-water cleansing cosmetic composition of the present invention preferably contains the carboxylic acid-modified silicone (A) within a range of 0.1 to 15 mass %.

Note that "mass %" of the present specification is synonymous with "weight %", and is based on the total mass (total weight) of the oil-in-water cleansing cosmetic composition of the present invention, unless otherwise specified.

The oil agent (B) is preferably one or more types selected from hydrocarbon oils, silicone oils, and fatty acid esters.

The oil-in-water cleansing cosmetic composition of the present invention preferably contains water (C) within a range of 25 to 90 mass %.

The pH of the oil-in-water cleansing cosmetic composition of the present invention is preferably 6.0 to 9.5.

The oil-in-water cleansing cosmetic composition of the present invention may further contain (E) a nonionic surfactant with an HLB of 4 to 14.

The nonionic surfactant (E) with an HLB of 4 to 14 is preferably selected from a group consisting of polyoxyethylene fatty acid esters, polyoxyethylene fatty acid glyceryls, and fatty acid polyoxyethylene alkyl ethers.

If the oil-in-water cleansing cosmetic composition of the present invention further contains the nonionic surfactant (E) with an HLB of 4 to 14, the compounded amount thereof is preferably within a range of 0.1 to 8 mass %.

The oil-in-water cleansing cosmetic composition of the present invention may further contain (F) insoluble particles.

If the oil-in-water cleansing cosmetic composition of the present invention further contains the insoluble particles (F), the compounded amount thereof is preferably 10 mass % or less.

Effects of the Invention

The oil-in-water cleansing cosmetic composition according to the present invention quickly blends with makeup grime, has a high makeup removing effect, and has excellent stability. Here, "stable" means uniform without causing phase separation over time.

Further, the oil-in-water cleansing cosmetic of the present invention contains water, and therefore can provide a refreshing feel during use.

Furthermore, oil-in-water cleansing cosmetic composition of the present invention has reduced stickiness even though an oil agent is included.

DESCRIPTION OF THE PREFERRED EMBODIMENT

As a result of extensive studies, the present inventors discovered that a stable cleansing cosmetic composition that is suitable for makeup removal applications can be provided by blending a carboxylic acid-modified silicone that is liquid at 50° C. into an oil-in-water composition, thereby achieving the present invention.

The oil-in-water cleansing cosmetic composition of the present invention is in the form of an oil-in-water type when not in use, in other words, when not in contact with the skin, but immediately phase inverts into the water-in-oil type and becomes the water-in-oil form upon contact with the skin. Thereby, blending with makeup is quick, and thus makeup is favorably removed.

In particular, the oil-in-water cleansing cosmetic composition of the present invention, even when the amount of an oil phase is relatively low, immediately produces a phase inversion when applied to the skin, and therefore, blends quickly with makeup such that the makeup can be favorably removed.

The oil-in-water cleansing cosmetic composition of the present invention is preferable for makeup removal. The oil-in-water cleansing cosmetic composition of the present invention is preferably not a skin cleaning material used to clean skin to which no makeup has been applied.

Hereinafter, the oil-in-water cleansing cosmetic composition of the present invention will be further described in detail.

[Carboxylic Acid Modified Silicone]

The cosmetic composition of the present invention contains at least one type of (A) a carboxylic acid-modified silicone that is liquid at 50° C. By including the carboxylic acid-modified silicone (A), the phase quickly inverts into a water-in-oil type when applied to the skin while maintaining a stable emulsified condition in an oil-in-water type, and exhibits an excellent makeup removal effect. Note that, the (A) carboxylic acid-modified silicone may be in a liquid form at room temperature 50° C. and one atmosphere, and for example, it may be a solid at room temperature (25° C.).

The carboxylic acid-modified silicone (A) included in the cosmetic composition of the present invention is not particularly limited so long as it is an organosiloxane in which at least one carboxyl group-containing organic group is introduced to a side chain or an end, so long as the carboxylic acid-modified silicone is liquid at 50° C. Preferably, the carboxyl group-containing organic group is introduced into the side chain of the organosiloxane.

Therefore, examples of the carboxylic acid-modified silicone (A) include those in which a carboxyl group-containing organic group is grafted on a silicone main chain; those in which a carboxyl group-containing organic group is added to one end of a silicone main chain; those in which a carboxyl group-containing organic group is added to both ends of a silicone main chain; those in which a carboxyl group-containing organic group is added to both ends of a silicone main chain, and the carboxyl group-containing organic group is grafted; those in which a silicone chain (including a siloxane macromonomer bonded by a silalkylene bond) and a carboxyl group-containing organic group is grafted on a silicone main chain; those in which a silicone main chain or an end has a siloxane modifying group having a carbosiloxane dendrimer structure and a carboxyl group-containing organic group, and optionally, carboxylic acid-modified silicone having a long-chain alkyl group having 6 or more carbon atoms; and the like. The carboxylic acid-modified silicone in which a silicone main chain is grafted with a carboxyl group-containing organic group is most suitable. Note that when the carboxylic acid-modified silicone (A) has a long chain alkyl group, the compounding stability with an organic oil agent such as a hydrocarbon oil or the like may be improved.

A linking group may be present between a carboxyl group and a silicon atom, and examples of the linking group include divalent or higher valent organic groups such as an alkylene group which may have a hetero atom and a polyoxyalkylene group, but are not particularly limited. Furthermore, the (n-1) carboxyl group may be carboxylic acid-modified silicone bonded to a silicon atom by an n-valent linking group (n is a number of equal to or larger than 3). Specifically, a silicone having a carboxyl group on a main chain or side chain of a silicone via the following linking group is included in the carboxylic acid-modified silicone (A) of the present invention.

Organopolysiloxane having a silicon-bonded carboxyl group-containing organic group as disclosed in Japanese Translation of PCT International Application Publication No. 11-504665:

[Formula 3]

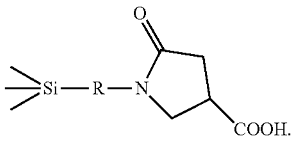

(wherein, R represents a $C_1$-$C_{12}$ alkylene group, a $C_1$-$C_{12}$ alkyleneoxy group, an oxygen atom, a sulfur atom, —NH—, or —NR'— (R' is a $C_1$-$C_6$ alkyl group), or a divalent group containing a combination of these), Organopolysiloxane having any of the following carboxyl group-containing organic groups, disclosed in Japanese Unexamined Patent Application Publication No. 2002-114849:

[Formula 4]

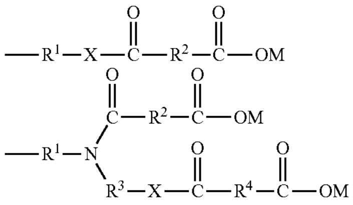

(wherein, $R^1$ to $R^{24}$ represent linear or branched chain alkylene groups, alkenylene groups, or arylene groups having 2 to 22 carbon atoms, which are the same or different and may have a substituent containing a hetero atom, X represents —O— or NH—, and M represents a hydrogen atom), Organopolysiloxane having a carboxyl group-containing organic group disclosed in Japanese Translation of PCT International Application Publication No. 2005-524747:

[Formula 5]

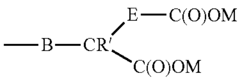

(wherein B represents an alkylene residue substituted with one or more alkyl groups having 2 to 30 carbon atoms and optionally 1 to 30 carbon atoms, R' represents a hydrogen atom or an alkyl group having 1 to 30 carbon atoms, E is either not present or has 1 to 5 carbon atoms, and preferably 1 to 3 carbon atoms, and optionally, an alkylene residual group is substituted by one or more alkyl groups having 1 to 30 carbon atoms; and M is a hydrogen atom), Organopolysiloxane having the following carboxyl group-containing organic group represented by the following average composition formula, disclosed in Japanese Unexamined Patent Application Publication No. 2009-263643:

[Formula 6]

$$R^1_aR^2_bR^3_cSiO_{(4-a-b-c)/2} \quad (1)$$

(wherein, $R^1$ is a group selected from an alkyl group having 1 to 30 carbon atoms, a phloroalkyl group having 1 to 30 carbon atoms, an aryl group having 6 to 30 carbon atoms, and an aralkyl group having 6 to 30 carbon atoms, $R^2$ is a group represented by Formula (2) below, and when c is 0, $R^2$ is bonded to at least one end of the organopolysiloxane,

[Formula 7]

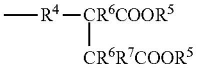

(2)

(wherein $R^4$ is a divalent hydrocarbon group having or not having an oxygen atom having 2 to 20 carbon atoms, $R^5$ is a hydrogen atom, $R^6$s each independently represent a hydrogen atom or an alkyl group having 1 to 6 carbon atoms, and $R^7$ is a hydrogen atom or an alkyl group having 1 to 6 carbon atoms), $R^3$ is a group represented by Formula (3) below:

[Formula 8]

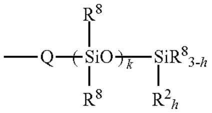

(3)

(wherein, $R^2$ is as described above, $R^8$s each independently represent the group selected from an alkyl group having 1 to 30 carbon atoms, a fluoroalkyl group having 1 to 30 carbon atoms, an aryl group having 6 to 30 carbon atoms, and an aralkyl group having 6 to 30 carbon atoms, Q is $C_dH_{2d}$ (here, d is an integer of 1 to 5, preferably an integer of 2 to 4) or an oxygen atom, k is an integer of 0 to 500, preferably 1 to 100, and more preferably 5 to 60, and h is an integer of 0 to 3 and preferably 0).

Particularly suitable examples of the carboxylic acid-modified silicone (A) used in the present invention include carboxylic acid-modified silicones in which at least one silicone atom on a side chain or an end of a silicone main chain is bonded to a carboxyl group-containing organic group as expressed by a general formula: $—R^1—(OR^2)p-(O)w-R^3—COOH$, (where $R^1$ represents a linear or branched alkylene group having 2 to 22 carbon atoms, $R^2$ represents a linear or branched alkylene group having 2 to 4 carbon atoms, $R^3$ represents a bond (-) or a linear or branched alkylene group having 1 to 22 carbon atoms, p represents a number from 0 to 200, and w represents a number of 0 or 1).

In the general formula representing the carboxyl group-containing organic group, $R^1$ is a linear or branched alkylene group having 2 to 22 carbon atoms, preferably a linear alkylene group having 2 to 12 carbon atoms, particularly preferably a linear alkylene group having 2 to 10 carbon atoms, and examples thereof include ethylene, propylene, trimethylene, butylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups.

In addition, examples of the linear or branched alkylene group having 2 to 4 carbon atoms of $R^2$ include ethylene, propylene, trimethylene, and butylene groups, and an ethylene group is particularly preferable.

Examples of the linear or branched alkylene group having 1 to 22 carbon atoms of $R^3$ include ethylene, ethylethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups. Among these, those having 1 to 12 carbon atoms, particularly those in which the sum of the carbon atoms of $R^1$ and $R^3$ is 2 to 22, are preferable.

p represents the number of 0 to 200, and the number of 0 to 20 is preferable, and the number of 0 to 10 is particularly preferable. In addition, w represents the number of 0 or 1, and is preferably 0. Note that, when p and w are both 0, the carboxyl group-containing organic group is represented by the structural formula $—(C_nH_{2n})—COOH$, and the carboxyl group-containing organic group preferably has a structure in which one carboxyl group is bonded to a silicon atom via a linear or branched alkylene group having 3 to 44 carbon atoms. In the formula, n is a number of 3 to 44, preferably a number of 3 to 20, and particularly preferably a number of 3 to 16.

An example of the carboxylic acid-modified silicone (A) used in the present invention includes organopolysiloxanes as expressed by the following structural formula (1):

[Formula 9]

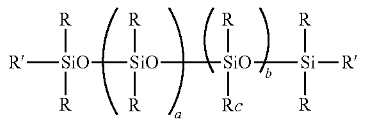

(1)

(where Rc represents a carboxyl group-containing organic group represented by a general formula: $—R^1—(OR^2)p-(O)w-R^3—COOH$, R represents the same or different alkyl or alkoxy group or phenyl group having 1 to 22 carbon atoms), R' is Rc or R, and each of a and b is a number in the range of 0 or more, and a+b is a number in the range of 0 to 1000. However, when b=0, at least one of the R' is Rc. In particular, the carboxylic acid-modified silicone disclosed in Japanese Unexamined Patent Application Publication No. 8-109263 and some of (other than those having a siloxane dendron structure) of the carboxylic acid-modified silicone disclosed in PCT International Publication No. WO 2009/22621 are represented by the structural formula (1) and are included in the carboxylic acid-modified silicone suitably used in the present invention.

Suitable examples of the carboxylic acid-modified silicone represented by structural formula (1) include carboxylic acid-modified silicone in which a+b is a number in the range 0 to 500, particularly, b>0, and a carboxyl group-containing organic group represented by the general formula: $—R^1—(OR^2)p-(O)w-R^3—COOH$ is grafted with the silicone main chain, and carboxylic acid-modified silicone in which b=0, and R' at both ends of the silicone main chain is a carboxyl group-containing organic group represented by the general formula: $—R^1—(OR^2)p-(O)w-R^3—COOH$. In the present invention, particularly suitable carboxylic acid-modified silicone is carboxylic acid-modified silicone having a large number of carboxyl group-containing organic groups in the side chain moiety, and it is preferable that b>a, and it is more suitable that b>0 and a=0. "b>a" means that more than half of the side chain moieties have siloxane units having a carboxyl group-containing organic group, and a+b is preferably a number in the range of 1 to 500. Furthermore, when a=0, if b>0, all of the siloxane units in the side chain moiety having a carboxyl group-containing organic group, and b is most preferably a number in a range of 1 to 200 or a number in a range of 1 to 50.

In structural formula (1), R is preferably a methyl group, an alkoxy group, or a phenyl group, but from the perspective of compounding stability with an organic oil agent such as a hydrocarbon oil or the like, R may have a long chain alkyl group with 6 to 22 carbon atoms in a portion. A degree of modification by the carboxyl group-containing organic group is not particularly limited, and if a+b is a number in the range of 0 to 500, it is preferable to have an average of 2 to 100 of the carboxyl group-containing organic groups in the molecule, including a case where the carboxyl group-containing organic group is bonded to both ends of the silicone main chain.

In the present invention, such carboxylic acid-modified silicone can be manufactured by known methods such as a method of subjecting dimethylpolysiloxane having a Si—H group and an unsaturated carboxylic acid ester compound to addition reaction under a platinum catalyst and to saponification to form carboxylic acid; a method of subjecting dimethylpolysiloxane having a Si—H group to addition reaction of unsaturated carboxylic acid silyl ester or allyloxycarboxylic acid silyl ester under a platinum catalyst, and to obtain the desired product by hydrolysis after the reaction; and a method of obtaining carboxylic acid-modified silicone at both ends by an equilibrium reaction using bis(hydroxycarbonylethyl) tetramethyldisiloxane with cyclic siloxane and an acidic catalyst (Silicone Handbook, edited by Kunio Ito, NIKKAN KOGYO SHIMBUN, LTD. pp. 166-167).

Furthermore, in the present invention, a commercially available carboxylic acid-modified silicone can be used as is or after removing a solvent, as the carboxylic acid-modified silicone as expressed by the structural formula (1). Specific examples thereof include BY16-880, BY16-750, FZ-3516, and ES-5800 Formulation Aid (manufactured by Dow Toray Co., Ltd.), TSF 4770, and TSF 4771 (manufactured by Momentive Performance Materials), X-22-162A, X-22-162C, X-22-3701E, and X-22-3710 (manufactured by Shin-Etsu Chemical Co., Ltd.), and the like.

Note that the carboxylic acid modified silicone (A) is preferably liquid at room temperature (25° C.). Note that the carboxylic acid modified silicone (A) is preferably liquid at room temperature (25° C.) and at 1 atmosphere.

The carboxylic acid modified silicone (A) is more preferably expressed by the following structural formula (2):

[Formula 10]

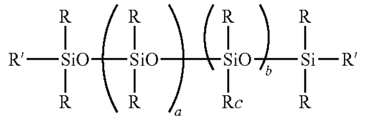

(2)

(Where Rc represents an organic group containing a carboxyl group as expressed by general formula: —$R^1$—$(OR^2)$p-(O)w-$R^3$—COOH, ($R^1$ represents a straight chain or branched chain alkylene group having 2 to 22 carbon atoms, $R^2$ represents a straight chain or branched chain alkylene group having 2 to 4 carbon atoms, $R^3$ represents a bond (-) or a straight chain or branched chain alkylene group having 1 to 22 carbon atoms, p represents a number from 0 to 200, and w represents a number of 0 or 1), R represents the same or a different alkyl or alkoxy group, having 1 to 22 carbon atoms, or phenyl group, R' is Rc or R, a and b each represent a positive number, where preferably a≥2 and b≥2, a+b is a number within a range of 2 to 20, preferably 2 to 15, and more preferably 2 to 10, and a/b is within a range of 0.3 to 3.0, preferably 0.3 to 2.5, more preferably 0.3 to 2.0, and even more preferably 0.5 to 2.0).

In the general formula representing the carboxyl group-containing organic group in the structural formula (2), $R^1$ is a linear or branched alkylene group having 2 to 22 carbon atoms, preferably a linear alkylene group having 2 to 12 carbon atoms, particularly preferably a linear alkylene group having 2 to 10 carbon atoms, and examples thereof include ethylene, propylene, trimethylene, butylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups.

In addition, examples of the linear or branched alkylene group having 2 to 4 carbon atoms of $R^2$ include ethylene, propylene, trimethylene and butylene groups, and an ethylene group is particularly preferable.

Examples of the linear or branched alkylene group having 1 to 22 carbon atoms of $R^3$ include ethylene, ethylethylene, propylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, and hexadecamethylene groups. Among these, those having 1 to 12 carbon atoms, particularly those in which the sum of the carbon atoms of $R^1$ and $R^3$ is 2 to 22 are preferable.

p represents the number of 0 to 200, and the number of 0 to 20 is preferable, and the number of 0 to 10 is particularly preferable. In addition, w represents the number of 0 or 1, and is preferably 0. Note that, when p and w are both 0, the carboxyl group-containing organic group is represented by the structural formula —$(C_nH_{2n})$—COOH, and the carboxyl group-containing organic group preferably has a structure in which one carboxyl group is bonded to a silicon atom via a linear or branched alkylene group having 3 to 44 carbon atoms. In the formula, n is a number of 3 to 44, preferably a number of 3 to 20, and particularly preferably a number of 3 to 16.

The (A) carboxylic acid-modified silicone represented by structural formula (2) is not particularly limited as long as the at least one carboxyl group-containing organic group is a side chain or the end introduced organosiloxane. Preferably, the carboxyl group-containing organic group is introduced into the side chain of the organosiloxane.

Therefore, examples of the (A) carboxylic acid-modified silicone represented by the structural formula (2) include those in which a silicone main chain is grafted with a carboxyl group-containing organic group as a side chain; a carboxyl group-containing organic group is added to one end of the silicone main chain; a carboxyl group-containing organic group is added to both ends of the silicone main chain; and a carboxyl group-containing organic group is added to both ends of the silicone main chain, and the carboxyl group-containing organic group is further grafted as a side chain, and optionally, carboxylic acid-modified silicone having a long-chain alkyl group having 6 or more carbon atoms can be exemplified. The carboxylic acid-modified silicone in which a silicone main chain is grafted with a carboxyl group-containing organic group is most suitable as a side chain. Note that when the carboxylic acid-modified silicone (A) has a long chain alkyl group, the compounding stability with an organic oil agent such as a hydrocarbon oil or the like may be improved.

The (A) carboxylic acid-modified silicone represented by the structural formula (2) is preferably carboxylic acid-modified silicone in which R' is R and a carboxyl group-containing organic group represented by the general formula: —$R^1$—$(OR^2)$p-(O)w-$R^3$—COOH is grafted with the silicone side chain; more preferably carboxylic acid-modified silicone in which R' is R and the silicone side chain has a plurality of the aforementioned carboxyl group-containing organic groups; and still more preferably carboxylic acid-modified silicone in which R' is R, the silicone side chain has a plurality of the aforementioned carboxyl group-containing organic groups, and a/b=1.

In structural formula (2), R is preferably a methyl group, an alkoxy group, or a phenyl group, but from the perspective of compounding stability with an organic oil agent such as a hydrocarbon oil or the like, R may have a long chain alkyl group with 6 to 22 carbon atoms in a portion.

In the present invention, such carboxylic acid-modified silicone can be manufactured by known methods such as a method of subjecting dimethylpolysiloxane having a Si—H group and an unsaturated carboxylic acid ester compound to addition reaction under a platinum catalyst and to saponification to form carboxylic acid; a method of subjecting dimethylpolysiloxane having a Si—H group to addition reaction of unsaturated carboxylic acid silyl ester or allyloxycarboxylic acid silyl ester under a platinum catalyst, and to obtain the desired product by hydrolysis after the reaction; and a method of obtaining carboxylic acid-modified silicone at both ends by an equilibrium reaction using bis(hydroxycarbonylethyl) tetramethyldisiloxane with cyclic siloxane and an acidic catalyst (Silicone Handbook, edited by Kunio Ito, NIKKAN KOGYO SHIMBUN, LTD. pp. 166-167). Furthermore, particularly, examples of the suitable carboxylic acid-modified silicone of the present invention include those available from the trade name ES-5800 Formulation Aid (available from Dow Toray Co., Ltd.), and the like.

The cosmetic composition of the present invention preferably contains the carboxylic acid modified silicone (A) within a range of 0.1 to 15 mass %, more preferably within a range of 0.5 to 10 mass %, and even more preferably within a range of 1.0 to 5 mass %, relative to the total mass of the cosmetic composition. If the amount of the carboxylic acid-modified silicone (A) is excessively low, the stability of an emulsion and the performance of ease of makeup removal are reduced, and if the amount is excessively high, phase inversion into a water-in-oil type is less likely to occur even when applied to the skin. Therefore, ease of blending with makeup grime is reduced.

[Oil Agent]

The cosmetic composition of the present invention includes at least one oil agent (B). The oil agent forms an oil phase in the cosmetic composition of the present invention. The cosmetic composition of the present invention can exhibit favorable removal performance with regard to makeup by including the oil agent (B).

The "oil agent" in the present invention is generally used as a component of a cosmetic composition, and is not particularly limited. The oil agent is usually liquid at room temperature, but may be a solid such as wax, or may be in the form of a highly viscous and viscous gum or paste, which will be described later.

The oil agent (B) is preferably at least one type that is liquid at 5° C. to 100° C. selected from a group consisting of silicone oils, fluorine-based oils, nonpolar organic compounds, and low polarity organic compounds. The oil agent (B) is particularly preferably one or more types selected from hydrocarbon oils, silicone oils, and fatty acid esters.

Silicone oils are hydrophobic, and their molecular structure may be cyclic, linear, or branched. The viscosities of silicone oils at 25° C. are usually in the range of 0.65 to 100,000 $mm^2/s$, preferably in the range of 0.65 to 10,000 $mm^2/s$.

Silicone oils include, for example, linear organopolysiloxanes, cyclic organopolysiloxanes, and branched organopolysiloxanes. Among these, linear organopolysiloxanes, cyclic organopolysiloxanes, and branched organopolysiloxanes that are volatile are preferable.

More specifically, examples of linear organopolysiloxanes include dimethylpolysiloxane capped at both molecular chain ends with trimethylsiloxy groups (dimethylsilicone having low viscosity such as 2 mPa·s or 6 mPa·s to high viscosity of 1,000,000 mPa·s), organohydrogenpolysiloxane, methylphenylpolysiloxane capped at both molecular chain ends with trimethylsiloxy groups, dimethylsiloxane/methylphenylsiloxane copolymer capped at both molecular chain ends with trimethylsiloxy groups, diphenylpolysiloxane capped at both molecular chain ends with trimethylsiloxy groups, dimethylsiloxane/diphenylsiloxane copolymer capped at both molecular chain ends with trimethylsiloxy groups, trimethylpentaphenyl trisiloxane, phenyl (trimethylsiloxy) siloxane, methyl alkyl polysiloxane capped at both molecular chain ends with trimethylsiloxy groups, dimethylpolysiloxane/methylalkylsiloxane copolymer capped at both molecular chain ends with trimethylsiloxy groups, dimethylsiloxane/methyl (3,3,3-trifluoropropyl) siloxane capped at both molecular chain ends with trimethylsiloxy groups, α,ω-dihydroxypolydimethylsiloxane, α,ω-diethoxypolymethylsiloxane, 1,1,1,3,5,5,5-heptamethyl-3-octyltrisiloxane, 1,1,1,3,5,5,5-heptamethyl-3-dodecyltrisiloxane, 1,1,1,3,5,5,5-heptamethyl-3-hexadecyltrisiloxane, tristrimethylsiloxymethylsilane, tristrimethylsiloxyalkylsilane, tetrakistrimethylsiloxysilane, tetramethyl-1,3-dihydroxydisiloxane, octamethyl-1,7-dihydroxytetrasiloxane, hexamethyl-1,5-diethoxytrisiloxane, hexamethyldisiloxane, octamethyltrisiloxane, higher alkoxy modified silicones, higher fatty acid modified silicones, dimethiconol and the like.

Examples of cyclic organopolysiloxanes include hexamethylcyclotrisiloxane (D3), octamethylcyclotetrasiloxane (D4), decamethylcyclopentasiloxane (D5), dodecamethylcyclotetrasiloxane (D6), 1,1-diethylhexamethylcyclotetrasiloxane, phenylheptamethylcyclotetrasiloxane, 1,1-diphenylhexamethylcyclotetrasiloxane, 1,3,5,7-tetravinyltetramethylcyclotetrasiloxane, 1,3,5,7-tetramethylcyclotetrasiloxane, 1,3,5,7-tetracyclohexyltetramethylcyclotetrasiloxane, tris(3,3,3-trifluoropropyl) trimethylcyclotrisiloxane, 1,3,5,7-tetra(3-methacryloxypropyl)tetramethylcyclotetrasiloxane, 1,3,5,7-tetra(3-acryloxypropyl)tetramethylcyclotetrasiloxane, 1,3,5,7-tetra(3-carboxypropyl)tetramethylcyclotetrasiloxane, 1,3,5,7-tetra(3-vinyloxypropyl)tetramethylcyclotetrasiloxane, 1,3,5,7-tetra(p-vinylphenyl)tetramethylcyclotetrasiloxane, 1,3,5,7-tetra[3-(p-vinylphenyl)propyl]tetramethylcyclotetrasiloxane, 1,3,5,7-tetra(N-acryloyl-N-methyl-3-aminopropyl)tetramethylcyclotetrasiloxane, 1,3,5,7-tetra(N,N-bis(lauroyl)-3-aminopropyl) tetramethylcyclotetrasiloxane, and the like.

Examples of the branched organopolysiloxane include methyltristrimethylsiloxysilane, ethyltristrimethylsiloxysilane, propyltristrimethylsiloxysilane, tetrakistrimethylsiloxysilane, and phenyltristrimethylsiloxysilane.

Examples of the fluorine-based oil include perfluoropolyether, perfluorodecalin, perfluorooctane, and the like.

As the nonpolar organic compound and the low polarity organic compound, a hydrocarbon oil and a fatty acid ester oil are preferable. Hydrocarbon oils are particularly preferred.

Examples of the hydrocarbon oil include liquid paraffin, light liquid isoparaffin, heavy liquid isoparaffin, petrolatum, n-paraffin, isoparaffin, isododecane, isohexadecane, polyisobutylene, hydrogenated polyisobutylene, polybutene, ozokerite, ceresin, microcrystalline wax, paraffin wax, polyethylene wax, polyethylene polypropylene wax, scralan, squalene, pristane, polyisoprene, and the like.

Examples of fatty acid ester oils include hexyldecyl octanoate, cetyl octanoate, isopropyl myristate, isopropyl palmitate, butyl stearate, hexyl laurate, myristyl myristate, oleyl oleate, decyl oleate, octyldodecyl myristate, hexyldecyl dimethyl octanoate, cetyl lactate, myristyl lactate, diethyl phthalate, dibutyl phthalate, lanolin acetate, propylene glycol dioleate, glyceryl tri-2-ethylhexanoate, trimethylolpropane tri-2-ethylhexanoate, ditrimethylolpropane triethylhexanoate, ditrimethylolpropane (isostearate/sebacate), trimethylolpropane trioctanoate, trimethylolpropane triisostearate, diisopropyl adipate, diisobutyl adipate, 2-hexyldecyl adipate, di-2-heptyl undecyl adipate, diisostearyl malate, hydrogenated castor oil monoisostearate, octyldodecyl isostearate, isopropyl isostearate, isocetyl isostearate, ethylene glycol di-2-ethylhexanoate, cetyl 2-ethylhexanoate, pentaerythritol tetra-2-ethylhexanoate, octyldodecyl gum esters, ethyl oleate, octyldodecyl oleate, neopentyl glycol dicaprate, triethyl citrate, 2-ethylhexyl succinate, dioctyl succinate, isocetyl stearate, diisopropyl sebacate, di-2-ethylhexyl sebacate, diethyl sebacate, dioctyl sebacate, dibutyl octyl sebacate, cetyl palmitate, octyldodecyl palmitate, octyl palmitate, 2-ethylhexyl palmitate, 2-hexyldecyl palmitate, 2-heptyl undecyl palmitate, cholesteryl 12-hydroxystearylate, dipentaerythritol fatty acid esters, 2-hexyldecyl myristate, ethyl laurate, 2-octyldodecyl N-lauroyl-L-glutamate, di-(cholesteryl/behenyl/octyldodecyl) N-lauroyl-L-glutamate, di-(cholesteryl/octyldodecyl) N-lauroyl-L-glutamate, di-(phytosteryl/behenyl/octyldodecyl) N-lauroyl-L-glutamate, di-(phytosteryl/octyldodecyl) N-lauroyl-L-glutamate, N-lauroyl sarcosine isopropyl, diisostearyl malate, neopentyl glycol dioctanoate, isodecyl neopentanoate, isotridecyl neopentanoate, isostearyl neopentanoate, isononyl isononanoate, isotridecyl isonononanoate, octyl isonononanoate, isotridecyl isonononanoate, diethyl pentanediol dineopentanoate, methyl pentanediol dineopentanoate, octyldodecyl neodecanoate, 2-butyl-2-ethyl-1,3-propanediol dioctanoate, pentaerythrityl tetraoctanoate, hydrogenated rosin pentaerythrityl, pentaerythrityl triethylhexanoate, dipentaerythrityl (hydroxystearate/stearate/rosinate), polyglyceryl tetraisostearate, polyglyceryl nonaisostearate-10, polyglyceryl deca(erucate/isostearate/lysinoleate)-8, diglyceryl oligoester (hexyl decanoate/sebacate), glycol distearate (ethylene glycol distearate), diisopropyl dimer linoleate, diisostearyl dimer linoleate, di-(isostearyl/phytostearyl) dimer dilinoleate, (phytostearyl/behenyl) dimer dilinoleate, (phytostearyl/isostearyl/cetyl/stearyl/behenyl) dimer dilinoleate, dimer dilinoleyl dimer dilinoleate, dimer dilinoleyl diisostearate, dimer dilinoleyl hydrogenated rosin condensate, hardened castor oil dimer dilinoleate, hydoxyalkyl dimer dilinoleyl ethers, glyceryl triisostearate, glyceryl trimyristate, glyceryl triisopalmitate, glyceryl trioctanoate, glyceryl trioleate, glyceryl diisostearate, glyceryl tri-(caprylate/caprate), glyceryl tri-(caprylate/caprate/myristate/stearate), glyceryl hydrogenated rosin glyceryl, hydrogenated rosin triglyceride (hydrogenated ester gum), rosin triglyceride (ester gum), glyceryl eicosanedioate behenate, glyceryl di-2-heptyl undecanoate, diglyceryl isostearate myristate, cholesteryl acetate, cholesteryl nonanoate, cholesteryl stearate, cholesteryl isostearate, cholesteryl oleate, cholesteryl 12-hydroxystearate, macadamia nut oil fatty acid cholesteryl, macadamia nut oil fatty acid phytosteryl, phytosteryl isostearate, soft lanolin fatty acid cholesteryl, hard lanolin fatty acid cholesteryl, long-chain branched fatty acid cholesteryl, long-chain α-hydroxy fatty acid cholesteryl, octyldodecyl ricinoleate, lanolin fatty acid octyldodecyl, octyldodecyl erucate, hardened castor oil isostearate, avocado oil fatty acid ethyl, lanolin fatty acid isopropyl, corn oil, safflower oil, sunflower oil, avocado oil, rice germ oil, wheat germ oil, almond oil, soybean oil, rapeseed oil, sesame oil, camelia oil, camelia sasanqua oil, persic oil, olive oil, gold tea oil, perilla seed oil, mink oil, castor oil, flax oil, evening primrose oil, star aniseed oil, and the like.

For example, higher alcohols having 10 to 30 carbon atoms can be used as the low polarity organic compound. Examples of higher alcohols having 10 to 30 carbon atoms include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, sitosterol, phytosterol, lanosterol, lanolin alcohol, hydrogenated lanolin alcohol, and the like.

The compounded amount of the oil agent (B) in the cosmetic composition of the present invention is, based on the total mass of the cosmetic composition, 3 to 80 mass %, preferably 3 mass % or more, more preferably 5 mass % or more, even more preferably 10 mass % or more, and yet even more preferably 15 mass % or more, and preferably 80 mass % or less, more preferably 60 mass % or less, even more preferably 50 mass % or less, and yet even more preferably 40 mass % or less. The compounded amount of the oil agent (B) in the cosmetic composition of the present invention is preferably 5 to 60 mass %, more preferably 10 to 50 mass %, and even more preferably 15 to 40 mass %, based on the total mass of the cosmetic composition. If the amount of the oil agent (B) is excessively low, blending with makeup grime tends to be slow and makeup removal performance tends to be reduced, while if the amount is excessively high, stickiness tends to be felt after use.

[Water]

The cosmetic composition of the present invention contains water (C). The water forms an aqueous phase in the cosmetic composition of the present invention.

The compounded amount of the water (C) in the cosmetic composition of the present invention is not particularly limited, but is preferably 25 mass % or more, more preferably 30 mass % or more, and even more preferably 35 mass % or more, and preferably 90 mass % or less, more preferably 80 mass % or less, and even more preferably 70 mass % or less, based on the total mass of the cosmetic composition. The compounded amount of the water (C) in the cosmetic composition of the present invention is preferably 25 to 90 mass %, more preferably 30 to 80 mass %, and even more preferably 35 to 70 mass %, based on the total mass of the cosmetic composition.

[Basic Compound]

The cosmetic composition of the present invention contains at least one basic compound (D).

The basic compound (D) used in the present invention is not particularly limited so long as the compound exhibits basicity when dissolved in water, and various types of inorganic compounds and organic compounds can be used. One or more types of the basic compound (D) may be blended.

Examples of the organic compound include monoethanolamine, triethanolamine, 2-amino-2-methyl-1,3-propanediol, aminomethylpropanol, arginine, and guanidine.

Examples of the inorganic compounds include sodium hydroxide, sodium carbonate, potassium hydroxide, potassium carbonate, calcium hydroxide, calcium carbonate, ammonia, and the like. Among these, potassium hydroxide can be particularly suitably used.

The compounded amount of the basic compound (D) in the cosmetic composition of the present invention is not particularly limited, but in the case of a monovalent base per 1 mol of the carboxylic acid group included in the blended carboxylic acid modified silicone, the carboxylic acid group/monovalent base (molar ratio) is preferably 1/0.5 to 1/1.5. Specifically, the blending amount of the base is preferably 0.01 to 2.5 mass %, more preferably 0.05 to 2.0 mass %, still more preferably 0.1 to 1.5 mass % based on the total mass of the cosmetic composition.

The pH of the cosmetic composition of the present invention may be acidic or alkaline, but is preferably weakly acidic to weakly alkaline, and is specifically preferably within a range of 6.0 to 9.5, more preferably within a range of 6.5 to 9.0, and even more preferably within a range of 7.0 to 8.5.

When the pH of the cosmetic composition of the present invention is weakly alkaline, a carboxylic acid modified site of the carboxylic acid modified silicone (A) is anionized, such that the carboxylic acid modified silicone (A) can favorably exhibit a function as a surfactant.

The basic compound (D) in the cosmetic composition of the present invention may be neutralized in advance with the carboxylic acid modified silicone (A) in the cosmetic composition of the present invention, and then blended into the cosmetic composition as a carboxylic acid modified silicone salt.

[Ionic Surfactant]

The cosmetic composition of the present invention may contain an ionic surfactant, and if an ionic surfactant is included, the amount is 10 mass % or less, and preferably 5 mass % or less, based on the total mass of the cosmetic composition. If the amount of the ionic surfactant exceeds 10 mass %, when the cosmetic composition of the present invention is applied to the skin, phase inversion from the oil-in-water type to the water-in-oil type is difficult, and blending with makeup grime is slow. The ionic surfactant herein is different from the carboxylic acid modified silicone (A).

Examples of the ionic surfactant can include carboxylic acid salts having an alkyl group having 10 to 20 carbon atoms, sulfates, sulfonates, phosphates, and other anionic surfactants, cationic surfactants, amphoteric surfactants, and the like. However, a carboxylic acid salt is preferably used, which is neutralized by the neutralizing ability of skin and loses hydrophilicity when applied to the skin in the same manner as the carboxylic acid modified silicone (A). An ionic surfactant other than the carboxylic acid salt is preferably substantially not included.

In the present invention, the "substantially not included" described above means less than 1 mass % of the total mass of the cosmetic composition of the present invention can be included. However, a lower amount is advantageous, which is preferably 0.5 mass % or less, and more preferably 0.1 mass % or less.

[Nonionic Surfactant]

The cosmetic composition of the present invention can contain at least one type of (E) nonionic surfactant having an HLB of 4 to 14.

The HLB of the nonionic surfactant (E) is preferably 5 to 13, and more preferably 6 to 12.

The nonionic surfactant (E) with an HLB of 4 to 14 can function as an auxiliary emulsifier. Therefore, when the cosmetic composition of the present invention contains component (E), the stability of the cosmetic composition of the present invention can be further improved.

Furthermore, when the cosmetic composition of the present invention contains the nonionic surfactant (E) having an HLB of 4 to 14, the cosmetic composition of the present invention is easy to wash off with water or lukewarm water after use, and thus usability is further improved. On the other hand, even if the cosmetic composition of the present invention does not contain the nonionic surfactant (E) having an HLB of 4 to 14, the cosmetic composition of the present invention can be removed by wiping off after use.

Specific examples of nonionic surfactants that can be used as component (E) include: polyglyceryl-4 stearate, polyglyceryl-10 distearate, polyglyceryl-2 oleate, and other polyglycerol fatty acid esters; PEG-10 hydrogenated castor oil, PEG-20 hydrogenated castor oil, and other polyoxyethylene hardened castor oils; PEG-5 stearate, PEG-6 isostearate, and other polyoxyethylene fatty acid esters; Ceteth-2, Oleth-2, Steareth-15, and other polyoxyethylene alkyl ethers; Steareth-12 stearate and Laureth-10 isostearate, and other fatty acid polyoxyethylene alkyl ethers; PEG-6 glyceryl isostearate, PEG-20 glyceryl triisostearate, PEG-20 glyceryl tristearate, PEG-7 glyceryl cocoate, and other polyoxyethylene fatty acid glyceryls; PEG-20 hardened castor oil isostearate, PEG-20 hardened castor oil triisostearate, and other fatty acid polyoxyethylene hardened castor oils; polyoxyethylene sorbitan fatty acid esters, polyoxyethylene-polyoxypropylene copolymers, ethers of polyoxyethylene-polyoxypropylene copolymers and long chain alcohols, and ethers of polybutylene glycol-polyglycerin copolymers and long chain alcohols, and the like. Of these, a polyoxyethylene fatty acid ester, polyoxyethylene fatty acid glyceryl, fatty acid polyoxyethylene alkyl ether can be preferably used.

When the nonionic surfactant (E) having an HLB of 4 to 14 has a fatty acid residual group in a molecule, the fatty acid residual group is preferably a residual group of a higher fatty acid having 10 to 22 carbon atoms, such as myristic acid, palmitic acid, stearic acid, isostearic acid, oleic acid, or the like. Examples of commercially available products that can be preferably used include "Cetiol HE-JP" (PEG-7 glyceryl cocoate; manufactured by BASF; HLB 12), "UNIOX GT-201S" (PEG-20 glyceryl tristearate; manufactured by NOF Corporation; HLB 10.4), "EMALEX PEIS-6EX" (PEG-6 isostearate; manufactured by NIHON EMULSION Co., Ltd.; HLB 9), "EMALEX SWS-12" (Steareth-12 stearate; manufactured by NIHON EMULSION Co., Ltd.; HLB 8), and the like.

The compounded amount of the nonionic surfactant (E) having an HLB of 4 to 14 in the cosmetic composition of the present invention is not particularly limited, but is preferably 0.1 to 8 mass %, more preferably 0.5 to 7 mass %, and even more preferably 1 to 6 mass %, based on the total mass of the cosmetic composition.

[Insoluble Particles]

The cosmetic composition of the present invention may contain at least one type of insoluble particles (F). The insoluble particles (F) are insoluble in oil and/or water, and are preferably non-swelling in oil or water. By including the insoluble particles (F), a scrubbing effect can be achieved, for example. Furthermore, the stability of the cosmetic composition of the present invention can also be improved by blending the insoluble particles (F). The particle diameter of the insoluble particles (F) is preferably 1 μm to 200 μm.

So long as the insoluble particles (F) can stably be present in the cosmetic composition of the present invention, the shape of the particles, such as spherical, plate-like, spindle-like, needle-like, irregular, and the like, the structure of the particles, such as porous, non-porous, and the like, and the material and origin of the particles, such as inorganic, organic, natural, synthetic, and the like, are not particularly limited. Examples of such particles include inorganic pigments, organic pigments, photoluminescent pigments, constitutional powders, pigment powders, composite powders, seed kernel grains/shell grains, and the like. Specific examples include titanium oxide, zinc oxide, iron blue, ultramarine blue, silicic anhydride, magnesium carbonate, calcium carbonate, aluminum hydroxide, chromium hydroxide, carbon black, aluminum silicate, magnesium silicate, magnesium aluminum silicate, mica, smectite, bentonite, kaolin, synthetic mica, synthetic sericite, sericite, talc, alumina, silicon carbide, barium sulfate, boron nitride, bismuth oxychloride, titanated mica, iron oxide-coated mica, iron oxide-coated titanated mica, organic pigment-coated titanated mica, aluminum powder, N-acyllysine, polystyrene powder, nylon powder, polymethyl methacrylate powder, polymethyl silsesquioxane powder, organopolysiloxane elastomer powder, apricot kernel grains, peach kernel grains, walnut shell grains, and the like. In particular, seed kernel grains and shell grains, such as apricot kernel grains, peach kernel grains, walnut shell grains, and the like, are preferred when included as scrubbing agents. Note that when used as a scrubbing agent, the insoluble particles (F) include may be casein or other protein powders, wheat flour, chitin, chitosan, other polysaccharide powders, or the like, polyethylene powders, polystyrene powders, nylon powders, crystalline cellulose, organically modified clay minerals, cross-linked sodium polyacrylate, starch sodium acrylate graft copolymers, pumice, magnesium aluminum silicate, silicic anhydride, laponite colloidal alumina, clay minerals, salt, hydrous magnesium silicate, hydrous potassium aluminum silicate, hydrous aluminum silicate, or the like.

The compounded amount of the insoluble particles (F) in the cosmetic composition of the present invention is not particularly limited, but is preferably 0.1 to 5 mass %, more preferably 0.3 to 3 mass %, and even more preferably 0.5 to 1 mass %, based on the total mass of the cosmetic composition.

[Polyhydric Alcohol]

The cosmetic composition of the present invention may contain at least one polyhydric alcohol (G).

By including the polyhydric alcohol (G), the feel during use of the cosmetic composition of the present invention can be adjusted.

Examples of the polyhydric alcohol (G) include sorbitol, xylitol, propylene glycol, dipropylene glycol, 1,3-butylene glycol, glycerin, diglycerin, polyethylene glycol, and the like, which can be used alone or in combination of two or more types. Of these, propylene glycol, dipropylene glycol, 1,3-butylene glycol, glycerin, diglycerin, or a combination thereof is preferred.

The compounded amount of the polyhydric alcohol (G) in the cosmetic composition of the present invention is not particularly limited, but is preferably 0.3 to 30 mass %, more preferably 0.5 to 25 mass %, and even more preferably 1 to 20 mass %, based on the total mass of the cosmetic composition.

(Water-Soluble Thickening Agent)

The cosmetic composition of the present invention may contain at least one type of a water-soluble thickening agent (H).

General-purpose thickening agents for cosmetic compositions can be used as the water-soluble thickening agent (H). For example, a hydrophilic organic polymer can be used as the water-soluble thickening agent (H).

By including the water-soluble thickening agent (H), the viscosity and feel during use of the cosmetic composition of the present invention can be adjusted, and storage stability can be further improved.

Examples of the water-soluble thickening agent (H) include carboxyvinyl polymers, sodium polyacrylate, polyethylene glycol, acrylic acid alkyl methacrylate copolymers, polyoxyethylene polyoxypropylene block copolymer, polyvinyl alcohol, polyvinylpyrrolidone, polyvinyl methyl ether, methyl cellulose, ethyl cellulose, hydroxyethyl cellulose, hydroxypropyl cellulose, hydroxypropyl methylcellulose, cationized cellulose, sodium alginate, propylene glycol ester alginate, guar gum, locust bean gum, carrageenan, xanthan gum, dextrin, bentonite, modified potato starch, hydroxypropyl starch phosphoric acid, and other starch modified products, and the like. A carboxyvinyl polymer, acrylic acid alkyl methacrylate copolymer, polyvinyl alcohol, polyvinylpyrrolidone, and hydroxypropyl methyl cellulose are preferred. These water-soluble thickening agents can be used independently or in combination of two or more.

The compounded amount of the water-soluble thickening agent (H) in the cosmetic composition of the present invention is not particularly limited, but is preferably 0.01 to 5 mass %, more preferably 0.05 to 2 mass %, and even more preferably 0.1 to 2 mass %, based on the total mass of the cosmetic composition.

[Optional Components]

Other components ordinarily used in cosmetic compositions can be added to the cosmetic composition of the present invention within a range that does not hinder an effect of the present invention. Examples thereof include: particles other than component (F), moisturizing agents other than component (G), thickening agents other than component (H), antiseptic agents, antimicrobial agents, perfumes, salts, antioxidants, pH adjusting agents other than component (D), chelating agents, refreshing agents, anti-inflammatory agents, physiologically active components (skin lightening agents, cell activating agents, rough skin improving agents, circulation promoters, skin astringents, anti-seborrheic agents, and the like), vitamins, amino acids, nucleic acids, hormones, inclusion compounds, and the like. Other components are not particularly limited.

[Producing Method]

The cosmetic composition of the present invention can be manufactured by mixing the carboxylic acid modified silicone (A) that is liquid at 50° C., a predetermined amount of the oil agent (B), the water (C) and the basic compound (D). The manufacturing process of the cosmetic composition of the present invention is arbitrary, and is not particularly limited so long as each of the aforementioned components can be mixed to prepare an oil-in-water cleansing cosmetic composition containing components (A) to (D). If necessary, at least one type selected from a group consisting of the aforementioned components (E) to (H) may be further mixed.

[How to Use]

The cosmetic composition of the present invention, which may be in the form of a cream, gel, or liquid, and the cosmetic composition of the present invention may be used for cleaning or removing makeup.

Examples of makeup as a target for removal by the cosmetic composition of the present invention includes makeup cosmetic compositions such as foundation, mascara, lipstick, eye shadow, and the like. The cosmetic composition of the present invention is preferred for cleaning makeup that is difficult to remove by water or hot water alone or by a surfactant type cleaning material such as face wash soaps, face wash foams, and the like.

The cosmetic composition of the present invention can be preferably used to remove makeup on the skin by applying onto the skin. Therefore, the cosmetic composition of the present invention is preferably an oil-in-water skin cleansing cosmetic composition.

The cosmetic composition of the present invention can be used, for example, by wiping off with a cotton, non-woven material, or the like after applying onto a predetermined site on the skin and then blending with sebum grime or makeup grime. Furthermore, after applying onto the predetermined site on the skin, the cosmetic composition of the present invention may be blended with sebum grime or makeup grime, and then washed off by water or lukewarm water. The cosmetic composition of the present invention is preferably washed off by water or lukewarm water after being blended with sebum grime or makeup grime.

The cosmetic composition of the present invention is in the form of an oil-in-water composition and the water configuring a continuous phase comes into direct contact with the skin. Therefore, the cosmetic composition is not sticky and provides a fresh and refreshing feel during use, particularly at the beginning of use, despite containing an oil agent. Furthermore, the cosmetic composition of the present invention can provide a pleasant feel during use as if oil were melting on the skin, by an oil phase and an aqueous phase inverting during use.

The cosmetic composition of the present invention is usually stored in an appropriate container, such as a glass or plastic container or the like, but if necessary, can also be impregnated in a carrier in advance in the form of a sheet for wiping. The carrier is not particularly limited so long as the carrier contains a material that can sufficiently impregnated with the cosmetic composition. Examples can include paper, non-woven materials, gauze, absorbent cotton, urethane sheets, sponge flakes, and the like. Of these, nonwoven materials itself having oily component adsorption properties are particularly preferred. Furthermore, the impregnation ratio of the cosmetic composition is preferably the maximum amount within a range in which liquid does not drip, and the amount is dependent on the material, which can be easily confirmed by preliminary experiments.

A sheet impregnated with the cosmetic composition of the present invention is normally packaged, together with some extra cosmetic composition, in a highly airtight and lightweight packaging form. Preferred specific examples of such a packaging form include laminated films having an aluminum layer and a polyethylene terephthalate layer or other resin film, and the like.

The cosmetic composition of the present invention is stable and can be stored over a long period of time.

EXAMPLES

Hereinafter, the present invention will be described in more detail based on examples, but the present invention is not limited to these examples.

Synthesis Example 1

230.67 g of trimethylsilyl undecylenate and 0.042 g of a platinum-1,3-divinyl-1,1,3,3-tetramethyldisiloxane complex were put into a flask equipped with a stirrer, a reflux condenser, a dropping funnel, and a thermometer, and 129.33 g of Si—H siloxane expressed by the following general formula was dropped thereinto so as to maintain the range of 70 to 80° C.

[Formula 11]

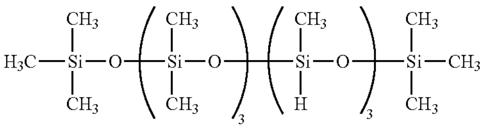

After dropping was complete, the mixture was aged for 2 hours at 110° C., and then the disappearance of the Si—H bond was confirmed by a hydrogen generation method. The low boiling point content was distilled off under reduced pressure. Thereafter, 90 g of deionized water was added, and the mixture was aged under reflux for 4 hours for deprotection. Thereafter, the low boiling point content was again removed under reduced pressure to obtain a compound 1. As a result of analysis, the chemical structure of the compound 1 was configured to be as expressed in the following chemical formula:

[Formula 12]

(Compound 1)

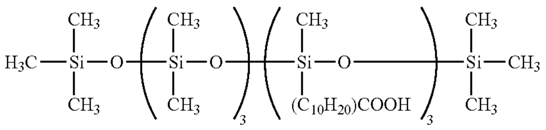

Synthesis Example 2

In a flask equipped with a stirrer, a reflux condenser, a dropping funnel, and a thermometer, 100 g of 1,1,1,3,5,5,5-heptamethyltrisiloxane, and 0.02 g of toluene solution of platinum-1,3-divinyl-1,1,3,3-tetramethyldisiloxane complex were added, and 105 g of trimethylsilyl undecylenate was added dropwise while keeping a temperature range of 70° C. to 100° C. After dropping was complete, the mixture was aged for 2 hours at 110° C., and then the disappearance of the Si—H bond was confirmed by a hydrogen generation method. The low boiling point content was distilled off under reduced pressure. Thereafter, water was added, aged at reflux for 4 hours, and deprotection was performed. Thereafter, the low boiling point content was again removed under reduced pressure to obtain a compound 2. As a result of the analysis, it was confirmed that the chemical structure of the compound 2 is shown in the following chemical formula:

[Formula 13]

(Compound 2)

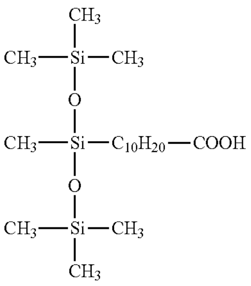

Synthesis Example 3

51.44 g of trimethylsilyl undecylenate and 0.035 g of a platinum-1,3-divinyl-1,1,3,3-tetramethyldisiloxane complex were put into a flask equipped with a stirrer, a reflux condenser, a dropping funnel, and a thermometer, and 128.56 g of Si—H siloxane expressed by the following general formula was dropped thereinto so as to maintain the range of 70 to 80° C.

[Formula 14]

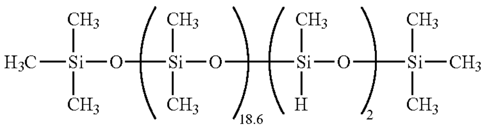

After dropping was complete, the mixture was aged for 2 hours at 110° C., and then the disappearance of the Si—H bond was confirmed by a hydrogen generation method. The low boiling point content was distilled off under reduced pressure. Thereafter, 90 g of deionized water was added, and the mixture was aged under reflux for 4 hours for deprotection. Thereafter, the low boiling point content was again removed under reduced pressure to obtain a compound 3. As a result of analysis, the chemical structure of the compound 3 was configured to be as expressed in the following chemical formula:

[Formula 15]

(Compound 3)

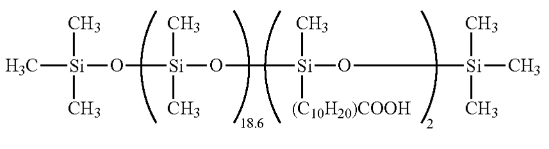

Examples 1 to 5 and Comparative Examples 1 to 4

Compositions of Examples 1 to 5 and Comparative Examples 1 to 4 were manufactured by the manufacturing method described below using the components shown in Table 1 and Table 2. The compounding amount of each component in Table 1 and Table 2 represent "mass %" ("weight %") unless otherwise specified.

(Producing Method)

(1) Components of phase A are mixed.
(2) Components of phase B are mixed.
(3) The mixture of the components in the phase B is added little to the mixture of the components in the phase A at normal room temperature to prepare a gel emulsion.
(4) Components in a phase C are mixed with the gel emulsion to prepare a cosmetic composition.

TABLE 1

| Phase | Component | Example 1 | Example 2 | Example 3 | Comparative Example 1 | Comparative Example 2 | Comparative Example 3 | Comparative Example 4 |
|---|---|---|---|---|---|---|---|---|
| A | Water | 1.00 | 1.00 | 1.00 | 1.00 | 1.00 | 20.00 | 1.00 |
| | Potassium hydroxide | 0.40 | 0.40 | 0.40 | 0.08 | 0.08 | — | 0.47 |
| | Arginine | — | — | — | — | — | 1.60 | — |
| | Glycerin | 12.00 | 12.00 | 12.00 | 12.00 | 12.00 | 12.00 | 12.00 |
| | Compound 1 | 2.00 | 2.00 | 2.00 | — | — | — | — |
| | Polyglyceryl-10 laurate *1 | 0.15 | 0.15 | 0.15 | 2.15 | 2.15 | 0.15 | 0.15 |
| | (Acrylates/alkyl acrylate (C10-30)) crosspolymer | — | — | — | — | — | 0.80 | — |
| | Isostearic acid | — | — | — | — | — | — | 2.00 |
| B | Liquid paraffin #70 | 30.00 | 40.00 | 15.00 | 30.00 | 15.00 | 30.00 | 40.00 |
| | PEG-20 glyceryl triisostearate *2 | 0.50 | 0.50 | 0.50 | 0.50 | 0.50 | 0.50 | 0.50 |
| | PEG-7 glyceryl cocoate *3 | 3.00 | 3.00 | 3.00 | 3.00 | 3.00 | 3.00 | 3.00 |
| C | Water | 44.25 | 34.25 | 59.25 | 44.57 | 59.57 | 25.65 | 34.18 |
| | 1,3-butylene glycol | 6.00 | 6.00 | 6.00 | 6.00 | 6.00 | 6.00 | 6.00 |
| | Phenoxyethanol | 0.30 | 0.30 | 0.30 | 0.30 | 0.30 | 0.30 | 0.30 |
| | Carbomer | 0.40 | 0.40 | 0.40 | 0.40 | 0.40 | — | 0.40 |
| | Total | 100.00 | 100.00 | 100.00 | 100.00 | 100.00 | 100.00 | 100.00 |
| | Evaluation results | | | | | | | |
| | pH | 7.20 | 7.39 | 7.33 | 6.05 | 5.95 | 7.42 | 8.07 |
| | Quickness of blending | ◎ | ◎ | ◎ | Δ | X | ○ | ◎ |
| | Makeup removal | ◎ | ◎ | ○ | Δ | X | Δ | Δ |
| | Level of lack of stickiness | ◎ | ○ | ◎ | ○ | ◎ | ○ | ○ |
| | Stability | ◎ | ◎ | ◎ | Δ | ○ | X | ○ |

*1 NIKKOL Decaglyn 1-L HLB 15.5
*2 UNIOX GT-20IS HLB 10.4
*3 CETIOL HE-JP HLB 12

TABLE 2

| Phase | Component | Example 4 | Example 5 |
|---|---|---|---|
| A | Water | 1.00 | 1.00 |
| | Potassium hydroxide | 0.36 | 0.19 |
| | Arginine | — | — |
| | Glycerin | 12.00 | 12.00 |
| | Compound 2 | 2.00 | |
| | Compound 3 | — | 2.00 |
| | Polyglyceryl-10 laurate | 0.15 | 0.15 |
| B | Liquid paraffin #70 | 40.00 | 40.00 |
| | PEG-20 glyceryl triisostearate | 0.50 | 0.50 |
| | PEG-7 glyceryl cocoate | 3.00 | 3.00 |
| C | Water | 34.29 | 34.46 |
| | 1,3-butylene glycol | 6.00 | 6.00 |
| | Phenoxyethanol | 0.30 | 0.30 |
| | Carbomer | 0.40 | 0.40 |
| | Total | 100.00 | 100.00 |

TABLE 2-continued

| Phase | Component | Example 4 | Example 5 |
|---|---|---|---|
| | Evaluation results | | |
| | pH | 7.79 | 6.54 |
| | Quickness of blending | ◎ | ◎ |
| | Makeup removal | ○ | ○ |
| | Level of lack of stickiness | ○ | ○ |
| | Stability | ◎ | ◎ |

Evaluation of Cleansing Cosmetic Composition

[Liquid Lipstick for Evaluation]

In order to evaluate the makeup removing effect of the cleansing cosmetic composition, a commercially available liquid lipstick (product name: LIQUID MATTE (color number: WILD CHILD) manufactured by HUDA BEAUTY) having the following component names indicated was used. This product is an extremely long-lasting liquid lipstick containing volatile oils (isododecane and cyclopentasiloxane) and film-forming resins (trimethylsiloxysilicate and polypropylene silsesquioxane).

Labeled Components for Commercial Liquid Lipstick LIQUID MATTE

"isododecane, cyclopentasiloxane, yellow beeswax, trimethylsiloxysilicic acid, polypropylsilsesquioxane, octyldodecanol, gistear dimonium hectorite, mica, alcohol, ethylvanillin, phenoxyethanol, fragrance, propylene carbonate, water, phospholipids, coffee seed extract, olive oil, ascorbyl palmitate, linoleic acid, retinol palmitate, tocopheryl acetate, lycopene, +/− titanium oxide, iron oxide, RED 6, RED 27, YELLOW 5, RED 40, BLUE 1"

The liquid lipstick for evaluation was applied to the inner side of a forearm of five people of a panel specializing in sensory evaluation in a circular shape having a 2 cm diameter by an attached applicator, allowed to dry for 30 minutes, and then the cleansing cosmetic compositions of Examples 1 to 5 and Comparative Examples 1 to 4 were evaluated.

(1) Quickness of Blending

Each of the cleansing cosmetic compositions of Examples 1 to 5 and Comparative Examples 1 to 4 was placed on a lipstick applicating part in the size of a pea and blended into the lipstick application while rotating with the index finger. When the entire lipstick application was lifted and blended into the cleansing cosmetic cleansing cosmetic composition, the number of times the finger was rotated was averaged between the five persons, and the cleansing cosmetic composition were judged as follows.

◎: Less than 10 times

○: More than 10 times, less than 15 times

Δ: More than 15 times, less than 20 times x: 20 times or more (2) Makeup Removal Each of the cleansing cosmetic compositions of Examples 1 to 5 and Comparative Examples 1 to 4 was placed on a lipstick applicating part in the size of a pea, blended into the lipstick application while rotating 10 times with the index finger, and then washed off with lukewarm water. The cleansing cosmetic compositions were judged as follows from the remaining condition of the lipstick.

◎: None remaining at all

○: Very little remains, but traces of lipstick color can be seen

Δ: Faded but the lipstick color remains.

x: Lipstick color is clearly seen (3) Level of Lack of Stickiness

After the aforementioned makeup removal evaluation, the evaluation expert panel was asked to evaluate the stickiness of the skin on the following three grades, and the total of the five evaluators' scores was used to make a judgment based on the following criteria.

3-Grade Evaluation

No stickiness, Grade 2

Slight stickiness, Grade 1

Sticky, Grade 0

Judgment Criteria

◎: Total of grades: 9 to 10

○: Total of grades: 6 to 8

Δ: Total of grades: 3 to 5 x: Total of grades: 2 or less (4) Stability

Each of the cleansing cosmetic compositions of Examples 1 to 5 and Comparative Examples 1 to 4 was placed in a 30 mL glass bottle, stored in a thermostatic bath at 50° C. for 7 days, observed for emulsification, and then evaluated for storage stability in accordance with the following criteria.

◎: No change

○: Slight reduction in whiteness and gloss

Δ: Uniform in appearance but reduced viscosity x: Creaming or separation of oil phase and aqueous phase is observed The results are shown in Tables 1 and 2.

The cleansing cosmetic compositions of Examples 1 to 5 in which a carboxylic acid-modified silicone is added quickly blended with makeup grime, favorably removed makeup after rinsing, and were stable with reduced stickiness. On the other hand, the cleansing cosmetic compositions of Comparative Examples 1 and 2, in which a hydrophilic nonionic surfactant (polyglyceryl-10 laurate) used in ordinary oil-in-water emulsions was used instead of the carboxylic acid-modified silicone used in Examples 1 to 5, required a long time to blend with makeup grime, and makeup removal after rinsing was not satisfactory. Furthermore, Comparative Example 3, in which emulsification was performed using an (acrylate/alkyl acrylate (C10 to 30)) cross-polymer instead of the carboxylic acid-modified silicone used in Examples 1 to 5, was not satisfactory from the perspective of makeup removal and stability. Furthermore, Comparative Example 4, in which isostearic acid was used for emulsification instead of the carboxylic acid-modified silicone used in Examples 1 to 5, was not satisfactory from the perspective of makeup removal, although blending with makeup grime was quick.

The invention claimed is:

1. An oil-in-water cleansing cosmetic composition, comprising:

(A) 0.1 to 15 mass % of a carboxylic acid-modified silicone that is liquid at 50° C.;

(B) 15 to 40 mass % of an oil agent relative to the total mass of the cosmetic composition;

(C) 30 to 80 mass % of water; and (D) 0.01 to 2.5 mass % of a basic compound;

wherein the carboxylic acid-modified silicone (A) is expressed by the following structural formula:

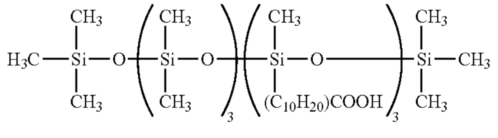

wherein an amount of an ionic surfactant other than the carboxylic acid-modified silicone (A) that is liquid at 50° C. is 10 mass % or less relative to the total mass of the cosmetic composition.

2. The oil-in-water cleansing cosmetic composition according to claim 1, wherein the carboxylic acid-modified silicone (A) is liquid at 25° C.

3. The oil-in-water cleansing cosmetic composition according to claim 1, wherein the carboxylic acid-modified silicone (A) is included within a range of 0.5 to 10 mass % relative to the total mass of the cosmetic composition.

4. The oil-in-water cleansing cosmetic composition according to claim 1, wherein the oil agent (B) is one or more type selected from the group consisting of hydrocarbon oils, silicone oils, and fatty acid esters.

5. The oil-in-water cleansing cosmetic composition according to claim 1, wherein the water (C) is included within a range of 35 to 70 mass % relative to the total mass of the cosmetic composition.

6. The oil-in-water cleansing cosmetic composition according to claim 1, wherein the pH is between 6.0 to 9.5.

7. The oil-in-water cleansing cosmetic composition according to claim 1, to further comprising:

(E) a nonionic surfactant with an HLB of 4 to 14.

8. The oil-in-water cleansing cosmetic composition according to claim 7, wherein the nonionic surfactant (E) with an HLB of 4 to 14 is selected from the group consisting of polyoxyethylene fatty acid esters, polyoxyethylene fatty acid glyceryls, and fatty acid polyoxyethylene alkyl ethers.

9. The oil-in-water cleansing cosmetic composition according to claim 7, wherein the nonionic surfactant (E) with an HLB of 4 to 14 is included within a range of 0.1 to 8 mass % relative to the total mass of the cosmetic composition.

10. The oil-in-water cleansing cosmetic composition according to claim 1, further comprising:

(F) insoluble particles.

11. The oil-in-water cleansing cosmetic composition according to claim 10, wherein the insoluble particles (F) are included within a range of 10 mass % or less relative to the total mass of the cosmetic composition.

12. The oil-in-water cleansing cosmetic composition according to claim 7, further comprising:

(F) insoluble particles.

13. The oil-in-water cleansing cosmetic composition according to claim 12, wherein the insoluble particles (F) are included within a range of 10 mass % or less relative to the total mass of the cosmetic composition.

14. The cosmetic composition according to claim 1, wherein the carboxylic acid-modified silicone (A) is included within a range of 1 to 5 mass % relative to the total mass of the cosmetic composition.

* * * * *